United States Patent
Koch et al.

(10) Patent No.: US 11,759,614 B2
(45) Date of Patent: Sep. 19, 2023

(54) ENHANCED STYLET FOR DRUG DEPOT INJECTOR

(71) Applicant: Warsaw Orthopedic, Inc., Warsaw, IN (US)

(72) Inventors: Brian D. Koch, Memphis, TN (US); Lloyd M. Snyder, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 165 days.

(21) Appl. No.: 17/023,746

(22) Filed: Sep. 17, 2020

(65) Prior Publication Data

US 2021/0236787 A1    Aug. 5, 2021

Related U.S. Application Data

(63) Continuation of application No. 16/132,808, filed on Sep. 17, 2018, now abandoned, which is a
(Continued)

(51) Int. Cl.
  *A61M 37/00* (2006.01)
  *A61M 5/315* (2006.01)
  *A61K 9/00* (2006.01)

(52) U.S. Cl.
  CPC ....... *A61M 37/0069* (2013.01); *A61K 9/0024* (2013.01); *A61M 5/31511* (2013.01)

(58) Field of Classification Search
  CPC .. A61M 37/00; A61M 5/178; A61M 37/0069; A61M 5/31511; A61K 9/0024
  See application file for complete search history.

(56) References Cited

U.S. PATENT DOCUMENTS

| 797,183 A | 10/1904 | Davis |
| 1,881,854 A | 10/1932 | Muir |

(Continued)

FOREIGN PATENT DOCUMENTS

| CN | 102056564 | 5/2011 |
| CN | 205073422 | 3/2016 |

(Continued)

OTHER PUBLICATIONS

U.S. Appl. No. 08/386,853, filed Feb. 10, 1995, Method and Device for Administering Analgesics.
(Continued)

*Primary Examiner* — Lauren P Farrar
*Assistant Examiner* — Hamza A Darb
(74) *Attorney, Agent, or Firm* — Knobbe Martens Olson & Bear LLP

(57) ABSTRACT

A pellet delivery system is provided that comprises a needle having an inner surface defining a passageway. The needle has a first portion that extends along a longitudinal axis and a curved second portion comprising an opening that is in communication with the passageway. The second portion extends transverse to the longitudinal axis. A pellet is positioned in the passageway. A plunger is slidably positioned in the passageway. The plunger comprises a shaft having a rounded tip configured to push the pellet through the first and second portions and out of the opening without the pellet becoming stuck within the passageway or the opening. Implants, systems, constructs, instruments and methods are disclosed.

20 Claims, 2 Drawing Sheets

Related U.S. Application Data continuation of application No. 14/949,118, filed on Nov. 23, 2015, now Pat. No. 10,076,650.

(56) References Cited

U.S. PATENT DOCUMENTS

| | | |
|---|---|---|
| 2,502,909 A | 4/1950 | Wick et al. |
| 2,513,014 A | 6/1950 | Fields |
| 2,751,907 A * | 6/1956 | Hickey ............. A61M 37/0069 604/60 |
| 2,883,984 A | 4/1959 | Candido, Jr. et al. |
| 3,016,895 A | 1/1962 | Sein |
| 3,520,299 A | 7/1970 | Tapper et al. |
| 3,620,216 A | 11/1971 | Szymanski |
| 4,044,989 A | 8/1977 | Basel et al. |
| 4,069,825 A | 1/1978 | Akiyama |
| 4,105,030 A | 8/1978 | Kercso |
| 4,164,560 A | 8/1979 | Folkman et al. |
| D262,156 S | 12/1981 | Grubelnig |
| 4,344,431 A | 8/1982 | Yolles |
| 4,346,709 A | 8/1982 | Schmitt |
| 4,402,308 A | 9/1983 | Scott |
| 4,427,015 A | 1/1984 | Redeaux |
| 4,451,253 A | 5/1984 | Harman |
| 4,516,593 A | 5/1985 | Muto |
| 4,525,156 A | 6/1985 | Benusa et al. |
| 4,531,938 A | 7/1985 | Kaye et al. |
| 4,559,054 A | 12/1985 | Bruck |
| 4,576,591 A | 3/1986 | Kaye et al. |
| 4,624,255 A | 11/1986 | Schenck et al. |
| 4,624,848 A | 11/1986 | Lee |
| 4,700,692 A | 10/1987 | Baumgartner |
| 4,742,054 A | 5/1988 | Naftchi |
| 4,762,515 A | 8/1988 | Grimm |
| 4,774,091 A | 9/1988 | Yamahira et al. |
| 4,781,695 A | 11/1988 | Dalton |
| 4,791,939 A | 12/1988 | Maillard |
| 4,819,684 A | 4/1989 | Zaugg et al. |
| 4,820,267 A | 4/1989 | Harman |
| 4,820,284 A | 4/1989 | Hauri |
| 4,855,335 A | 8/1989 | Neperud |
| 4,863,457 A | 9/1989 | Lee |
| 4,871,094 A | 10/1989 | Gall et al. |
| 4,892,538 A | 1/1990 | Patrick et al. |
| 4,900,304 A | 2/1990 | Fujioka et al. |
| 4,909,250 A | 3/1990 | Smith |
| 4,936,827 A | 6/1990 | Grimm et al. |
| 4,941,874 A | 7/1990 | Sandow et al. |
| 5,024,655 A | 6/1991 | Freeman et al. |
| 5,024,841 A | 6/1991 | Chu et al. |
| 5,131,401 A | 7/1992 | Westenskow et al. |
| D328,644 S | 8/1992 | Pericic |
| 5,135,493 A | 8/1992 | Peschke |
| 5,163,904 A | 11/1992 | Lampropoulos et al. |
| 5,180,716 A | 1/1993 | Yaksh et al. |
| 5,183,470 A | 2/1993 | Wettermann |
| 5,196,015 A | 3/1993 | Neubardt |
| 5,207,678 A | 5/1993 | Harms et al. |
| 5,212,162 A | 5/1993 | Missel et al. |
| 5,236,426 A | 8/1993 | Schottes et al. |
| 5,284,479 A | 2/1994 | De Jong |
| 5,312,351 A | 5/1994 | Gerrone |
| 5,330,768 A | 7/1994 | Park et al. |
| 5,337,735 A | 8/1994 | Salerno |
| D353,668 S | 12/1994 | Banks |
| 5,391,081 A | 2/1995 | Lampotang et al. |
| D362,064 S | 9/1995 | Smick |
| 5,449,351 A | 9/1995 | Zohmann |
| 5,466,219 A | 11/1995 | Lynn et al. |
| 5,474,558 A | 12/1995 | Neubardt |
| 5,484,403 A | 1/1996 | Yoakum et al. |
| 5,487,739 A | 1/1996 | Aebischer et al. |
| 5,514,101 A | 5/1996 | Schulz et al. |
| 5,520,660 A | 5/1996 | Loos et al. |
| 5,522,844 A | 6/1996 | Johnson |
| D373,823 S | 9/1996 | Baldwin |
| 5,558,637 A | 9/1996 | Allonen et al. |
| 5,571,882 A | 11/1996 | Velter |
| 5,622,940 A | 4/1997 | Ostroff et al. |
| 5,626,838 A | 5/1997 | Cavanaugh, Jr. |
| 5,633,002 A | 5/1997 | Stricker et al. |
| 5,694,920 A | 12/1997 | Abrams et al. |
| 5,695,463 A | 12/1997 | Cherif-Cheikh |
| 5,725,508 A | 3/1998 | Chanoch et al. |
| 5,733,572 A | 3/1998 | Unger et al. |
| 5,752,930 A | 5/1998 | Rise et al. |
| 5,756,127 A | 5/1998 | Grisoni et al. |
| 5,759,583 A | 6/1998 | Iwamoto et al. |
| 5,772,671 A | 6/1998 | Harmon |
| 5,827,234 A | 10/1998 | Loos et al. |
| 5,829,589 A | 11/1998 | Nguyen et al. |
| 5,830,130 A | 11/1998 | Janzen et al. |
| 5,834,001 A | 11/1998 | Dionne et al. |
| 5,868,789 A | 2/1999 | Huebner |
| 5,902,273 A | 5/1999 | Yang et al. |
| 5,928,130 A | 7/1999 | Schmidt |
| 5,928,158 A | 7/1999 | Aristides |
| 5,942,241 A | 8/1999 | Chasin et al. |
| 5,980,927 A | 11/1999 | Nelson et al. |
| 6,001,386 A | 12/1999 | Ashton et al. |
| 6,007,843 A | 12/1999 | Drizen et al. |
| 6,015,557 A | 1/2000 | Tobinick et al. |
| 6,036,978 A | 3/2000 | Gombotz et al. |
| 6,063,057 A | 5/2000 | Choh |
| 6,069,129 A | 5/2000 | Sandberg et al. |
| 6,083,534 A | 7/2000 | Wallach et al. |
| 6,086,614 A | 7/2000 | Mumme |
| 6,102,844 A | 8/2000 | Ravins et al. |
| 6,132,420 A | 10/2000 | Dionne et al. |
| 6,179,862 B1 | 1/2001 | Sawhney |
| 6,190,350 B1 | 2/2001 | Davis et al. |
| 6,193,692 B1 | 2/2001 | Harris et al. |
| 6,203,813 B1 | 3/2001 | Gooberman |
| 6,214,370 B1 | 4/2001 | Nelson et al. |
| 6,235,289 B1 | 5/2001 | Aoki et al. |
| 6,242,004 B1 | 6/2001 | Rault |
| 6,248,345 B1 | 6/2001 | Goldenheim et al. |
| 6,258,056 B1 | 7/2001 | Turley et al. |
| 6,273,877 B1 | 8/2001 | West et al. |
| 6,277,969 B1 | 8/2001 | Le et al. |
| 6,287,588 B1 | 9/2001 | Shih et al. |
| 6,298,256 B1 | 10/2001 | Meyer |
| 6,326,020 B1 | 12/2001 | Kohane et al. |
| 6,331,311 B1 | 12/2001 | Brodbeck et al. |
| 6,391,005 B1 | 5/2002 | Lum et al. |
| 6,413,245 B1 | 7/2002 | Yaacobi et al. |
| 6,428,804 B1 | 8/2002 | Suzuki et al. |
| 6,450,937 B1 | 9/2002 | Mercereau et al. |
| 6,461,631 B1 | 10/2002 | Dunn et al. |
| 6,471,688 B1 | 10/2002 | Harper et al. |
| 6,478,768 B1 | 11/2002 | Kneer |
| 6,478,776 B1 | 11/2002 | Rosenman et al. |
| 6,478,790 B2 | 11/2002 | Bardani |
| 6,488,649 B1 | 12/2002 | Lichten |
| 6,497,729 B1 | 12/2002 | Moussy et al. |
| 6,524,607 B1 | 2/2003 | Goldenheim et al. |
| 6,530,934 B1 | 3/2003 | Jacobsen et al. |
| 6,531,154 B1 | 3/2003 | Mathiowitz et al. |
| 6,534,081 B2 | 3/2003 | Goldenheim et al. |
| 6,551,290 B1 | 4/2003 | Elsberry et al. |
| 6,554,778 B1 | 4/2003 | Fleming |
| 6,565,541 B2 | 5/2003 | Sharp |
| 6,571,125 B2 | 5/2003 | Thompson |
| 6,582,441 B1 | 6/2003 | He et al. |
| 6,589,549 B2 | 7/2003 | Shih et al. |
| 6,594,880 B2 | 7/2003 | Elsberry |
| 6,616,946 B1 | 9/2003 | Meier et al. |
| 6,630,155 B1 | 10/2003 | Chandrashekar et al. |
| 6,632,457 B1 | 10/2003 | Sawhney |
| 6,648,849 B2 | 11/2003 | Tenhuisen et al. |
| 6,652,883 B2 | 11/2003 | Goupil et al. |
| 6,673,333 B1 | 1/2004 | Meade et al. |
| 6,676,971 B2 | 1/2004 | Goupil et al. |
| 6,710,126 B1 | 3/2004 | Hirt et al. |
| 6,723,741 B2 | 4/2004 | Jeon et al. |

(56) References Cited

U.S. PATENT DOCUMENTS

| | | |
|---|---|---|
| 6,723,814 B2 | 4/2004 | Meier et al. |
| 6,735,475 B1 | 5/2004 | Whitehurst et al. |
| 6,756,058 B2 | 7/2004 | Brubaker et al. |
| 6,773,714 B2 | 8/2004 | Dunn et al. |
| 6,837,865 B2 | 1/2005 | Kneer |
| 6,869,426 B2 | 3/2005 | Ganem |
| 6,916,308 B2 | 7/2005 | Dixon et al. |
| 6,921,541 B2 | 7/2005 | Chasin et al. |
| 6,936,270 B2 | 8/2005 | Watson et al. |
| 6,971,998 B2 | 12/2005 | Rosenman et al. |
| 6,974,462 B2 | 12/2005 | Sater |
| 6,982,089 B2 | 1/2006 | Tobinick |
| 6,993,375 B2 | 1/2006 | Burbank et al. |
| 7,001,892 B1 | 2/2006 | Chmielewski et al. |
| 7,012,106 B2 | 3/2006 | Yuan et al. |
| 7,018,384 B2 | 3/2006 | Skakoon |
| 7,070,583 B1 | 7/2006 | Higuchi et al. |
| 7,070,809 B2 | 7/2006 | Goupil et al. |
| 7,081,123 B2 | 7/2006 | Merboth et al. |
| 7,108,153 B2 | 9/2006 | Wood |
| 7,144,412 B2 | 12/2006 | Wolf et al. |
| 7,166,570 B2 | 1/2007 | Hunter et al. |
| 7,204,826 B2 | 4/2007 | Tremaglio et al. |
| 7,212,865 B2 | 5/2007 | Cory |
| 7,215,426 B2 | 5/2007 | Tsuyuki et al. |
| 7,220,281 B2 | 5/2007 | Lambrecht et al. |
| 7,223,289 B2 | 5/2007 | Trieu et al. |
| 7,229,441 B2 | 6/2007 | Trieu et al. |
| 7,235,043 B2 | 6/2007 | Gellman et al. |
| 7,252,651 B2 | 8/2007 | Haider et al. |
| 7,252,685 B2 | 8/2007 | Bindseil et al. |
| 7,276,477 B2 | 10/2007 | Osslund et al. |
| 7,287,983 B2 | 10/2007 | Ilan |
| 7,302,960 B2 | 12/2007 | Patzer |
| 7,317,091 B2 | 1/2008 | Lazar et al. |
| 7,318,840 B2 | 1/2008 | McKay |
| D561,896 S | 2/2008 | Jones |
| 7,329,259 B2 | 2/2008 | Cragg |
| 7,344,716 B2 | 3/2008 | Di Mauro et al. |
| 7,355,008 B2 | 4/2008 | Stavenhagen et al. |
| 7,357,792 B2 | 4/2008 | Newton et al. |
| 7,361,168 B2 | 4/2008 | Makower et al. |
| 7,367,978 B2 | 5/2008 | Drewry et al. |
| D571,463 S | 6/2008 | Chesnin |
| 7,400,930 B2 | 7/2008 | Sharkey et al. |
| 7,585,280 B2 | 9/2009 | Wilson et al. |
| 7,618,370 B2 | 11/2009 | Choi et al. |
| D606,190 S | 12/2009 | Pruitt |
| 7,637,279 B2 | 12/2009 | Amley et al. |
| 7,700,100 B2 | 4/2010 | Johnson et al. |
| D616,095 S | 5/2010 | Kim |
| 7,727,954 B2 | 6/2010 | McKay |
| 7,741,273 B2 | 6/2010 | McKay |
| D624,653 S | 9/2010 | Boillat |
| 7,798,988 B2 | 9/2010 | Aubert et al. |
| D630,733 S | 1/2011 | Ahlgren |
| 7,955,301 B1 | 6/2011 | McKay |
| 7,998,108 B2 | 8/2011 | Nazzaro et al. |
| 8,029,458 B2 | 10/2011 | Cherif-Cheikh et al. |
| 8,029,478 B2 | 10/2011 | Zanella |
| 8,084,582 B2 | 12/2011 | Dahiyat et al. |
| 8,088,119 B2 | 1/2012 | Saal et al. |
| 8,092,424 B2 | 1/2012 | Mueller et al. |
| 8,221,358 B2 | 7/2012 | McKay |
| 8,246,571 B2 | 8/2012 | Simonton et al. |
| 8,267,895 B2 | 9/2012 | McKay |
| 8,337,453 B2 | 12/2012 | Lind |
| 8,357,388 B2 | 1/2013 | McKay |
| 8,481,064 B2 | 7/2013 | McKay |
| 8,485,180 B2 | 7/2013 | Smutney et al. |
| 8,585,655 B2 | 11/2013 | Bierman |
| 8,608,705 B2 | 12/2013 | Peters et al. |
| 8,652,092 B2 | 2/2014 | Bussmann |
| 8,702,677 B2 | 4/2014 | Simonton et al. |
| 8,715,223 B2 | 5/2014 | McKay |
| 8,790,293 B2 | 7/2014 | Nazzaro et al. |
| D711,542 S | 8/2014 | Pierson |
| 8,834,412 B2 | 9/2014 | Painchaud et al. |
| D715,929 S | 10/2014 | Khalaj |
| 8,992,458 B2 | 3/2015 | Singh et al. |
| 8,998,854 B2 | 4/2015 | McKay |
| 9,050,415 B2 | 6/2015 | Shetty et al. |
| D737,435 S | 8/2015 | Ha et al. |
| D751,702 S | 3/2016 | Eaton et al. |
| 9,271,754 B2 | 3/2016 | Ostrovsky et al. |
| 9,381,111 B2 | 7/2016 | Hickingbotham et al. |
| D782,037 S | 3/2017 | Osypka |
| 9,764,122 B2 | 9/2017 | Clay et al. |
| 9,775,978 B2 | 10/2017 | Clay et al. |
| D802,755 S | 11/2017 | Snyder |
| D802,756 S | 11/2017 | Snyder |
| D802,757 S | 11/2017 | Snyder et al. |
| 9,867,974 B2 | 1/2018 | Beebe et al. |
| D809,652 S | 2/2018 | Snyder et al. |
| 10,076,650 B2 | 9/2018 | Koch et al. |
| 10,080,877 B2 | 9/2018 | Clay et al. |
| 10,272,234 B2 | 4/2019 | Wetzel et al. |
| 10,342,966 B2 | 7/2019 | Shetty et al. |
| 10,384,048 B2 | 8/2019 | Clay et al. |
| 10,391,291 B2 | 8/2019 | Wallace et al. |
| 10,405,955 B2 | 9/2019 | Eisele et al. |
| 10,434,261 B2 | 10/2019 | Snyder |
| 10,478,603 B2 | 11/2019 | Clay et al. |
| 10,549,081 B2 | 2/2020 | Snyder |
| 10,668,262 B2 | 6/2020 | Jacome et al. |
| 10,856,907 B2 | 12/2020 | Virden |
| 10,940,300 B2 | 3/2021 | Mellejor et al. |
| 11,166,798 B2 | 11/2021 | Eisele et al. |
| 11,273,266 B2 | 3/2022 | Daftary et al. |
| 11,413,442 B2 | 8/2022 | Snyder |
| 11,464,958 B2 | 10/2022 | Clay et al. |
| 11,478,587 B2 | 10/2022 | Snyder |
| 11,504,513 B2 | 11/2022 | Clay et al. |
| 2001/0005785 A1 | 6/2001 | Sachse |
| 2001/0020147 A1 | 9/2001 | Staniforth et al. |
| 2001/0031940 A1 | 10/2001 | Loos |
| 2001/0033867 A1 | 10/2001 | Ahern et al. |
| 2001/0043915 A1 | 11/2001 | Frey |
| 2002/0009454 A1 | 1/2002 | Boone et al. |
| 2002/0022800 A1 | 2/2002 | O'Holloran et al. |
| 2002/0077521 A1 | 6/2002 | Green et al. |
| 2002/0082583 A1 | 6/2002 | Lerner |
| 2002/0090398 A1 | 7/2002 | Dunn et al. |
| 2002/0116022 A1 | 8/2002 | Lebouitz et al. |
| 2002/0198527 A1 | 12/2002 | Muckter |
| 2003/0004491 A1 | 1/2003 | Tenhuisen et al. |
| 2003/0009235 A1 | 1/2003 | Manrique et al. |
| 2003/0023310 A1 | 1/2003 | Lubock et al. |
| 2003/0036673 A1 | 2/2003 | Schmidt |
| 2003/0039613 A1 | 2/2003 | Unger et al. |
| 2003/0045808 A1 | 3/2003 | Kaula et al. |
| 2003/0144570 A1 | 7/2003 | Hunter et al. |
| 2003/0171637 A1 | 9/2003 | Terwilliger et al. |
| 2003/0171954 A1 | 9/2003 | Guerin et al. |
| 2003/0185873 A1 | 10/2003 | Chasin et al. |
| 2003/0204191 A1 | 10/2003 | Sater et al. |
| 2003/0224033 A1 | 12/2003 | Li et al. |
| 2004/0015133 A1 | 1/2004 | Karim |
| 2004/0015149 A1 | 1/2004 | Palasis |
| 2004/0034357 A1 | 2/2004 | Beane et al. |
| 2004/0054338 A1 | 3/2004 | Bybordi et al. |
| 2004/0064088 A1 | 4/2004 | Gorman et al. |
| 2004/0064193 A1 | 4/2004 | Evans et al. |
| 2004/0065615 A1 | 4/2004 | Hooper et al. |
| 2004/0072799 A1 | 4/2004 | Li et al. |
| 2004/0082540 A1 | 4/2004 | Hermida Ochoa |
| 2004/0082908 A1 | 4/2004 | Whitehurst et al. |
| 2004/0098113 A1 | 5/2004 | Forsell et al. |
| 2004/0106914 A1 | 6/2004 | Coppeta et al. |
| 2004/0109893 A1 | 6/2004 | Chen et al. |
| 2004/0111118 A1 | 6/2004 | Hill et al. |
| 2004/0162574 A1 | 8/2004 | Viola |
| 2004/0214793 A1 | 10/2004 | Hermida Ochoa |
| 2004/0220545 A1 | 11/2004 | Heruth et al. |

(56) References Cited

U.S. PATENT DOCUMENTS

| | | |
|---|---|---|
| 2004/0220546 A1 | 11/2004 | Heruth et al. |
| 2004/0220547 A1 | 11/2004 | Heruth et al. |
| 2004/0220548 A1 | 11/2004 | Heruth et al. |
| 2004/0228901 A1 | 11/2004 | Trieu et al. |
| 2004/0229878 A1 | 11/2004 | DiMauro et al. |
| 2004/0249464 A1 | 12/2004 | Bindseil et al. |
| 2005/0025765 A1 | 2/2005 | DiMauro et al. |
| 2005/0043673 A1 | 2/2005 | Lieberman |
| 2005/0070843 A1 | 3/2005 | Gonzales |
| 2005/0074481 A1 | 4/2005 | Brekke et al. |
| 2005/0079202 A1 | 4/2005 | Chen et al. |
| 2005/0107756 A1 | 5/2005 | McCraw |
| 2005/0137579 A1 | 6/2005 | Heruth et al. |
| 2005/0142163 A1 | 6/2005 | Hunter et al. |
| 2005/0143689 A1 | 6/2005 | Ramsey, III |
| 2005/0152905 A1 | 7/2005 | Omoigui |
| 2005/0152949 A1 | 7/2005 | Hotchkiss et al. |
| 2005/0175709 A1 | 8/2005 | Baty, III et al. |
| 2005/0177118 A1 | 8/2005 | Hoganson et al. |
| 2005/0177135 A1 | 8/2005 | Hildebrand et al. |
| 2005/0178779 A1 | 8/2005 | Wood |
| 2005/0184264 A1 | 8/2005 | Tesluk et al. |
| 2005/0186261 A1 | 8/2005 | Avelar et al. |
| 2005/0197293 A1 | 9/2005 | Meilis et al. |
| 2005/0203542 A1 | 9/2005 | Weber et al. |
| 2005/0245906 A1 | 11/2005 | Makower et al. |
| 2005/0249775 A1 | 11/2005 | Falotico et al. |
| 2005/0228620 A1 | 12/2005 | Shipped |
| 2005/0278023 A1 | 12/2005 | Zwirkoski |
| 2005/0287218 A1 | 12/2005 | Chaouk et al. |
| 2005/0288789 A1 | 12/2005 | Chaouk et al. |
| 2006/0046960 A1 | 3/2006 | McKay et al. |
| 2006/0046961 A1 | 3/2006 | McKay et al. |
| 2006/0074422 A1 | 4/2006 | Story et al. |
| 2006/0084943 A1 | 4/2006 | Roseman et al. |
| 2006/0100622 A1 | 5/2006 | Jackson |
| 2006/0106361 A1 | 5/2006 | Muni et al. |
| 2006/0121032 A1 | 6/2006 | Dahiyat et al. |
| 2006/0148903 A1 | 7/2006 | Burch et al. |
| 2006/0153815 A1 | 7/2006 | Seyda et al. |
| 2006/0161114 A1 | 7/2006 | Perot et al. |
| 2006/0183786 A1 | 8/2006 | Wang |
| 2006/0189944 A1 | 8/2006 | Campbell et al. |
| 2006/0228391 A1 | 10/2006 | Seyedin et al. |
| 2006/0253100 A1 | 11/2006 | Burright et al. |
| 2006/0264839 A1 | 11/2006 | Veasey et al. |
| 2007/0005005 A1 | 1/2007 | Wang |
| 2007/0021358 A1 | 1/2007 | Edelman et al. |
| 2007/0043359 A1 | 2/2007 | Altarac et al. |
| 2007/0055378 A1 | 3/2007 | Ankney et al. |
| 2007/0066864 A1 | 3/2007 | Forde |
| 2007/0104769 A1 | 5/2007 | Feng et al. |
| 2007/0106247 A1 | 5/2007 | Burnett et al. |
| 2007/0118142 A1 | 5/2007 | Krueger et al. |
| 2007/0123863 A1 | 5/2007 | Winslow et al. |
| 2007/0129744 A1 | 6/2007 | Teichert et al. |
| 2007/0149992 A1 | 6/2007 | Teng |
| 2007/0156180 A1 | 7/2007 | Jaax et al. |
| 2007/0179474 A1 | 8/2007 | Cahill et al. |
| 2007/0185497 A1 | 8/2007 | Cauthen et al. |
| 2007/0202074 A1 | 8/2007 | Shalaby |
| 2007/0219564 A1 | 9/2007 | Rue et al. |
| 2007/0233038 A1 | 10/2007 | Pruit et al. |
| 2007/0243225 A1 | 10/2007 | McKay |
| 2007/0243228 A1 | 10/2007 | McKay |
| 2007/0244442 A1 | 10/2007 | Chowhan |
| 2007/0248639 A1 | 10/2007 | Demopulos et al. |
| 2007/0249632 A1 | 10/2007 | Zentner |
| 2007/0253994 A1 | 11/2007 | Hildebrand |
| 2007/0255281 A1 | 11/2007 | Simonton et al. |
| 2007/0255282 A1 | 11/2007 | Simonton et al. |
| 2007/0260184 A1 | 11/2007 | Justis et al. |
| 2007/0260201 A1 | 11/2007 | Prausnitz et al. |
| 2007/0265582 A1 | 11/2007 | Kaplan et al. |
| 2008/0004570 A1 | 1/2008 | Simonton et al. |
| 2008/0004703 A1 | 1/2008 | Trieu et al. |
| 2008/0009830 A1 | 1/2008 | Fujimoto et al. |
| 2008/0021074 A1 | 1/2008 | Cartt |
| 2008/0038351 A1 | 2/2008 | Beals et al. |
| 2008/0065029 A1 | 3/2008 | Racz |
| 2008/0077093 A1 | 3/2008 | Gratwohl et al. |
| 2008/0091207 A1 | 4/2008 | Truckai et al. |
| 2008/0097229 A1 | 4/2008 | Roy et al. |
| 2008/0102097 A1 | 5/2008 | Zanella |
| 2008/0125637 A1 | 5/2008 | Geist et al. |
| 2008/0139877 A1 | 6/2008 | Chu et al. |
| 2008/0208138 A1 | 8/2008 | Lim et al. |
| 2008/0215001 A1 | 9/2008 | Cowe |
| 2008/0228193 A1 | 9/2008 | Matityahu |
| 2008/0294039 A1 | 11/2008 | Jones et al. |
| 2009/0053211 A9 | 2/2009 | Lazar et al. |
| 2009/0088809 A1 | 4/2009 | Fisher et al. |
| 2009/0099597 A1 | 4/2009 | Isse |
| 2009/0131908 A1* | 5/2009 | McKay ............... A61B 17/3468 604/60 |
| 2009/0148500 A1 | 6/2009 | Lawter et al. |
| 2009/0177141 A1 | 7/2009 | Kucklick |
| 2009/0182267 A1 | 7/2009 | Painchaud et al. |
| 2009/0209804 A1 | 8/2009 | Seiler et al. |
| 2009/0246123 A1 | 10/2009 | Zanella et al. |
| 2009/0263319 A1 | 10/2009 | Wohabrebbi et al. |
| 2009/0263321 A1 | 10/2009 | McDonald et al. |
| 2009/0263441 A1 | 10/2009 | McKay |
| 2009/0263459 A1 | 10/2009 | King et al. |
| 2009/0263460 A1 | 10/2009 | McDonald |
| 2009/0264490 A1 | 10/2009 | Zanella et al. |
| 2009/0264491 A1 | 10/2009 | McKay et al. |
| 2009/0270797 A1 | 10/2009 | Aubert et al. |
| 2010/0015049 A1 | 1/2010 | Wohabrebbi |
| 2010/0106132 A1 | 4/2010 | Simonton |
| 2010/0106136 A1 | 4/2010 | Simonton |
| 2010/0106137 A1 | 4/2010 | Simonton et al. |
| 2010/0160375 A1 | 6/2010 | King |
| 2010/0163059 A1 | 7/2010 | Tierney et al. |
| 2010/0198140 A1 | 8/2010 | Lawson |
| 2010/0249750 A1 | 9/2010 | Racz |
| 2010/0331868 A1 | 12/2010 | Bardy |
| 2010/0331874 A1 | 12/2010 | Bardy |
| 2011/0098675 A1 | 4/2011 | Schmalz |
| 2011/0104233 A1 | 5/2011 | Drapeau |
| 2011/0106110 A1 | 5/2011 | McKay |
| 2011/0152755 A1 | 6/2011 | Schmalz |
| 2011/0182849 A1 | 7/2011 | Haddock et al. |
| 2011/0202011 A1 | 8/2011 | Wozencrift |
| 2011/0313393 A1 | 12/2011 | Zanella |
| 2012/0022568 A1 | 1/2012 | Koblish et al. |
| 2012/0142648 A1 | 6/2012 | Biggs et al. |
| 2012/0142747 A1 | 6/2012 | Wilsey et al. |
| 2013/0116556 A1 | 5/2013 | Racz |
| 2013/0178822 A1 | 7/2013 | Hickingbotham et al. |
| 2013/0211328 A1 | 8/2013 | Plumptre et al. |
| 2013/0261596 A1 | 10/2013 | McKay |
| 2014/0277459 A1 | 9/2014 | McCarthy |
| 2016/0263364 A1 | 9/2016 | Eisele et al. |
| 2016/0296739 A1 | 10/2016 | Cleveland |
| 2016/0354115 A1 | 12/2016 | Smith et al. |
| 2017/0231716 A1 | 8/2017 | Ahari et al. |
| 2017/0354811 A1 | 12/2017 | Clay et al. |
| 2018/0126090 A1 | 5/2018 | Snyder |
| 2019/0015653 A1 | 1/2019 | Koch et al. |
| 2019/0054253 A1 | 2/2019 | Kneer et al. |
| 2019/0247638 A1 | 8/2019 | Murphy |
| 2019/0255308 A1 | 8/2019 | Virden |
| 2019/0262115 A1 | 8/2019 | Eisele et al. |
| 2019/0374762 A1 | 12/2019 | Clay et al. |
| 2020/0030545 A1 | 1/2020 | Snyder |
| 2020/0078576 A1 | 3/2020 | Clay et al. |
| 2020/0171291 A1 | 6/2020 | Snyder |
| 2021/0000504 A1 | 1/2021 | Van Beek |
| 2021/0259736 A1 | 8/2021 | Hochmuth |
| 2021/0393935 A1 | 12/2021 | Richter et al. |
| 2022/0062608 A1 | 3/2022 | Kneer et al. |
| 2022/0117628 A1 | 4/2022 | Kuebler |

(56) References Cited

U.S. PATENT DOCUMENTS

| | | | |
|---|---|---|---|
| 2022/0143321 | A1 | 5/2022 | Daftary et al. |
| 2022/0143326 | A1 | 5/2022 | Daftary et al. |
| 2022/0203042 | A1 | 6/2022 | Daftary et al. |

FOREIGN PATENT DOCUMENTS

| | | |
|---|---|---|
| DE | 1955059 | 2/1967 |
| DE | 19640670 | 5/1998 |
| EP | 0 548 612 | 6/1993 |
| EP | 1 216 721 | 6/2002 |
| EP | 1 323 450 | 9/2004 |
| EP | 1 518 549 | 2/2007 |
| EP | 1 625 870 | 5/2008 |
| EP | 2 008 596 | 12/2008 |
| EP | 3 010 575 | 7/2021 |
| EP | 3 493 864 | 9/2021 |
| FR | 1 270 590 | 9/1961 |
| FR | 2 007 684 | 1/1970 |
| FR | 2 231 355 | 12/1974 |
| GB | 1379358 | 1/1975 |
| JP | 2006-509531 | 3/2006 |
| JP | 2009-160395 | 7/2009 |
| JP | 2011-087940 | 5/2011 |
| KR | 10-2006-0120103 | 11/2006 |
| WO | WO 93/20859 | 10/1993 |
| WO | WO 94/01166 | 1/1994 |
| WO | WO 1999/052573 | 10/1999 |
| WO | WO 2000/038574 | 7/2000 |
| WO | WO 2001/062272 | 8/2001 |
| WO | WO 2002/034116 | 5/2002 |
| WO | WO 2002/085188 | 10/2002 |
| WO | WO 2003/005961 | 1/2003 |
| WO | WO 2004/009776 | 1/2004 |
| WO | WO 2004/050688 | 6/2004 |
| WO | WO 2004/084819 | 10/2004 |
| WO | WO 2005/018468 | 3/2005 |
| WO | WO 2005/034998 | 4/2005 |
| WO | WO 2007/121288 | 10/2007 |
| WO | WO 2008/067362 | 6/2008 |
| WO | WO 2008/091777 | 7/2008 |
| WO | WO 2009/049823 | 4/2009 |
| WO | WO 2009/134314 | 11/2009 |
| WO | WO 2010/011526 | 1/2010 |
| WO | WO 2016/014300 | 1/2016 |
| WO | WO 2019/028138 | 2/2019 |
| WO | WO 2019/125457 | 6/2019 |

OTHER PUBLICATIONS

U.S. Appl. No. 08/775,528 (U.S. Pat. No. 5,980,927), filed Jan. 2, 1997 (Nov. 9, 1999) Method and Apparatus for Administering Analgesics, and Method for Making Same.
U.S. Appl. No. 09/291,571 (U.S. Pat. No. 6,214,370), filed Apr. 9, 1999 (Apr. 10, 2001), Method and Device for Administering Analgesics.
U.S. Appl. No. 10/932,878, filed Sep. 2, 2004, Controlled and Directed Local Delivery of Anti-Inflammatory Compositions.
U.S. Appl. No. 11/091,348, filed Mar. 28, 2005, Controlled and Directed Local Delivery of Anti-Inflammatory Compositions.
U.S. Appl. No. 11/932,442 (U.S. Pat. No. 8,029,478), filed Oct. 31, 2007 (Oct, 4, 2011), Implantable Device and Method for Delivering Drug Depots to a Site Beneath the Skin.
U.S. Appl. No. 13/220,086, filed Aug. 29, 2011, Implantable Device and Method for Delivering Drug Depots to a Site Beneath the Skin.
U.S. Appl. No. 11/942,820 (U.S. Pat. No. 8,221,358), filed Nov. 20, 2007 (Jul. 17, 2012), Devices and Methods for Deliverying Drug Depots to a Site Beneath the Skin.
U.S. Appl. No. 12/260,673, filed Oct. 29, 2008, Drug Delivery Device With Sliding Cartridge.
U.S. Appl. No. 12/260,683, filed Oct. 29, 2008, Drug Delivery System.
U.S. Appl. No. 12/260,700, filed Oct. 29, 2008, Drug Cartridge for Delivering a Drug Depot Comprising Superior and Inferior Covers.
U.S. Appl. No. 12/262,823 (U.S. Pat. No. 8,702,677), filed Oct. 31, 2008 (Apr. 22, 2014), Device and Method for Directional Delivery of a Drug Depot.
U.S. Appl. No. 12/507,197 (U.S. Pat. No. 8,715,223) filed Jul. 22, 2009 (May 6, 2014), Device and Method for Delivery Of a Drug Depot Near the Nerve.
U.S. Appl. No. 12/609,934, filed Oct. 30, 2009, Devices and Methods for Implanting a Plurality of Drug Depots Having One or More Anchoring Members.
U.S. Appl. No. 12/693,853 (U.S. Pat. No. 8,267,895, filed Jan. 26, 2020 (Sep. 18, 2012), Needle Guide System.
U.S. Appl. No. 12/694,329 (U.S. Pat. No. 7,955,301), filed Jan. 27, 2010 (Jun. 7, 2011), Injection Shut Off Valve With Pressure Actuator for Delivery of Compositions.
U.S. Appl. No. 12/695,899 (U.S. Pat. No. 8,998,854), filed Jan. 28, 2010 (Apr. 7, 2015), Catheter Devices and Drainage Systems for Delivering Therapeutic Agents.
U.S. Appl. No. 11/403,733 (U.S. Pat. No. 7,741,273), filed Apr. 13, 2006 (Jun. 22, 2010), Drug Depot Implant Designs.
U.S. Appl. No. 12/715,093 (U.S. Pat. No. 8,481,064), filed Mar. 1, 2010 (Jul. 9, 2013), Method for Delivering a Therapeutic Agent Comprising Injection of Microspheres.
U.S. Appl. No. 11/734,618 (U.S. Pat. No. 7,727,954), filed Apr. 12, 2007 (Jun. 1, 2010), Drug Depot Implant Designs.
U.S. Appl. No. 12/716,383 (U.S. Pat. No. 8,357,388), filed Mar. 3, 2010 (Jan. 22, 2013), Drug Depot Implant Designs and Methods of Implantation.
U.S. Appl. No. 12/861,857 (U.S. Pat. No. 8,246,571) filed Aug. 24, 2010 (Mar. 1, 2012), Drug Storage and Delivery Device Having a Retaining Member.
U.S. Appl. No. 13/309,725, filed Dec. 2, 2011, Methods for Delivering Clonidine Compositions in Biodegradable Polymer Carrier and Local Steroids to a Target Tissue Site.
U.S. Appl. No. 13/309,759, filed Dec. 2, 2011, Compositions and Methods for Delivering Clonidine to a Target Tissue Site.
U.S. Appl. No. 14/341,026 (U.S. Pat. No. 10,080,877) filed Jul. 25, 2014 (Sep. 25, 2018) Pellet Delivery Device.
U.S. Appl. No. 29/569,125 (U.S. Pat. No. D809,652) filed Jun. 23, 2016 (Feb. 6, 2018), Pellet Delivery Device.
U.S. Appl. No. 14/341,461 (U.S. Pat. No. 9,775,978) filed Jan. 28, 2016 (Oct. 3, 0217), Drug Delivery Device and Methods Having a Retaining Member.
U.S. Appl. No. 15/703,512 (U.S. Pat. No. 10,478,603) filed Sep. 13, 2017 (Nov. 19, 2019), Drug Delivery Device and Methods Having a Retaining Member.
U.S. Appl. No. 16/686,593, filed Nov. 18, 2019, Drug Delivery Device and Methods Having a Retaining Member.
U.S. Appl. No. 14,949,118 (U.S. Pat. No. 10,076,650) filed Nov. 23, 2015 (Sep. 18, 2018), Enhanced Stylet for Drug Depot Injector.
U.S. Appl. No. 16,132,808, filed Sep. 17, 2018, Enhanced Stylet for Drug Depot Injector.
U.S. Appl. No. 14/341,256 (U.S. Pat. No. 9,764,122), filed Jul. 25, 2014 (Sep. 19, 2017), Drug Delivery Device and Methods Having an Occluding Member.
U.S. Appl. No. 15/689,810 (U.S. Pat. No. 10,384,048), filed Aug. 29, 2017 (Aug. 20, 2019), Drug Delivery Device and Methods Having an Occluding Member.
U.S. Appl. No. 16/544,064, filed Aug. 19, 2019, Drug Delivery Device and Methods Having an Occluding Member.
U.S. Appl. No. 15/190,861 (U.S. Pat. No. 10/549,081), filed Jun. 23, 2016 (Feb. 4, 2020), Drug Delivery Device and Methods Having a Retaining Member.
U.S. Appl. No. 16/779,930, filed Feb. 3, 2020, Drug Delivery Device and Methods Having a Retaining Member.
U.S. Appl. No. 29/569,092 (U.S. Pat. No. D802,755) filed Jun. 23, 2016 (Nov. 14, 2017), Drug Pellet Cartridge.
U.S. Appl. No. 29/569,107 (U.S. Pat. No. D802,756) filed Jun. 23, 2016 (Nov. 14, 2017), Drug Pellet Cartridge.
U.S. Appl. No. 29/569,123 (U.S. Pat. No. D802,757) filed Jun. 23, 2016 (Nov. 14, 2017), Drug Pellet Cartridge.

(56) References Cited

OTHER PUBLICATIONS

U.S. Appl. No. 15/345,764 (U.S. Pat. No. 10/434,261), filed Nov. 8, 2016 (Oct. 8, 2019), Drug Pellet Delivery System and Method.
U.S. Appl. No. 16/590,654, filed Oct. 2, 2019, Drug Pellet Delivery System and Method.
Abd-Elsayed et al., "A Double-Blind Randomized Controlled Trial Comparing Epidural Clonidine vs Bupivacaine for Pain Control During and After Lower Abdominal Surgery", The Ochsner Journal, 2015, vol. 15, pp. 133-142.
U.S. Appl. No. 11/942,820 (U.S. Pat. No. 8,221,358), filed Nov. 20, 2007 (Jul. 17, 2012), Devices and Methods for Delivering Drug Depots to a Site Beneath the Skin.
U.S. Appl. No. 13/309,725, filed Dec. 2, 2021, Methods for Delivering Clonidine Compositions in Biodegradable Polymer Carrier and Local Steroids to a Target Tissue Site.
U.S. Appl. No. 14/341,461 (U.S. Pat. No. 9,775,978), filed Jan. 28, 2016 (Jan. 3, 0217), Drug Delivery Device and Methods Having a Retaining Member.
U.S. Appl. No. 15/703,512 (U.S. Pat. No. 10,478,603, filed Sep. 13, 2017 (Nov. 19, 2019), Drug Delivery Device and Methods Haveing a Retaining Member.
U.S. Appl. No. 15/345,764 (U.S. Pat. No. 10,434,261), filed Nov. 08, 2016 (Oct. 8, 2019), Drug Pellet Delivery System and Method.

\* cited by examiner

ENHANCED STYLET FOR DRUG DEPOT INJECTOR

INCORPORATION BY REFERENCE TO ANY PRIORITY APPLICATIONS

The present application is a continuation of U.S. patent application Ser. No. 16/132,808, filed Sep. 17, 2018, now abandoned, which is a continuation of U.S. patent application Ser. No. 14/949,118, filed Nov. 23, 2015 and issued as U.S. Pat. No. 10,076,650, which is hereby incorporated by reference in its entirety for all purposes.

TECHNICAL FIELD

The present disclosure generally relates to medical devices for the delivery of drug depots, and more particularly to an enhanced stylet for a pellet injector.

BACKGROUND

Drugs may be delivered to patients by a variety of methods including oral, intravenous, intramuscular, inhalation, topical or subcutaneous delivery. The drug may be delivered directly or locally to the treatment site (e.g., intrathecally, intraspinally, intraarticularly, etc.). The method of delivery chosen depends upon, among other things, the condition being treated, and the desired therapeutic concentration of the drug to be achieved in the patient and the duration of drug concentration that must be maintained.

Drug pellets, such as, for example, drug depots have been developed, which allow a drug to be introduced or administered to sites beneath the skin of a patient. Drug depot release the drug over a period of time. Drug depots allow the drug to be released from the depot in a relatively uniform dose over weeks, months or even years. Administering drugs using drug depots is becoming especially important and popular in modulating the immune, inflammation and/or pain responses in treatment of chronic conditions including rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, and the like.

Drug depots are typically inserted into a treatment site beneath the skin of a patient by use of a two-piece device that comprises a cannula or needle and a stylet or plunger that pushes the drug depot through the cannula or needle. The device requires an incision to be made through the skin using a separate instrument (e.g., scalpel). The cannula or needle may be inserted through the incision. The drug depot is inserted through the cannula or needle, and the stylet or plunger is used to push the implant to the end of the cannula or needle. The cannula or needle and stylet or plunger are then withdrawn completely, leaving the drug depot at the implant site.

Typically, the cannula or needle is an epidural Tuohy needle that has a curved tip and a stylet or plunger that comprises a flat tip is used to push the drug depot(s) through the cannula or needle. However, the flat tip of the stylet or plunger limits the amount that the tip can enter the curved tip of the Tuohy needle, thus preventing the stylet or plunger from reaching the opening at the curved end of the Tuohy needle. This may result in one or more drug depots becoming jammed in the curved end of the Tuohy needle, since the stylet or plunger cannot push the drug depots all the way through the Tuohy needle. This disclosure describes an improvement over these prior technologies.

SUMMARY

In one embodiment, a drug depot delivery system is provided. The delivery system comprises a needle having an inner surface defining a passageway. The needle comprises a first portion that extends along a longitudinal axis and a curved second portion comprising an opening that is in communication with the passageway. The second portion extends transverse to the longitudinal axis. A drug depot can be a pellet that is positioned in the passageway. A plunger is slidably positioned in the passageway. The plunger comprises a shaft having a rounded tip configured to push the drug depot through the first and second portions and out of the opening without the drug depot becoming stuck within the passageway or the opening. In some embodiments, systems, implants, constructs, instruments and methods are disclosed.

In one embodiment, a method of delivering a drug depot is provided. The method comprising creating an incision and inserting a needle of a drug depot delivery system through the incision so as to form a pathway to a target site. The needle comprising an inner surface defining a passageway, a first portion that extends along a longitudinal axis and a curved second portion comprising an opening that is in communication with the passageway. The second portion extending transverse to the longitudinal axis. The method also comprises positioning a drug depot in the passageway and moving a plunger of the delivery system in the passageway such that a rounded tip of the plunger pushes the drug depot through the first and second portions, out of the opening and into the patient adjacent to the target site. The rounded tip of the plunger is also used to push drug depots out of the opening after delivery of a first drug depot without the subsequent drug depots getting stuck.

BRIEF DESCRIPTION OF THE DRAWINGS

The present disclosure will become more readily apparent from the specific description accompanied by the following drawings, in which.

DETAILED DESCRIPTION

Figure 1:
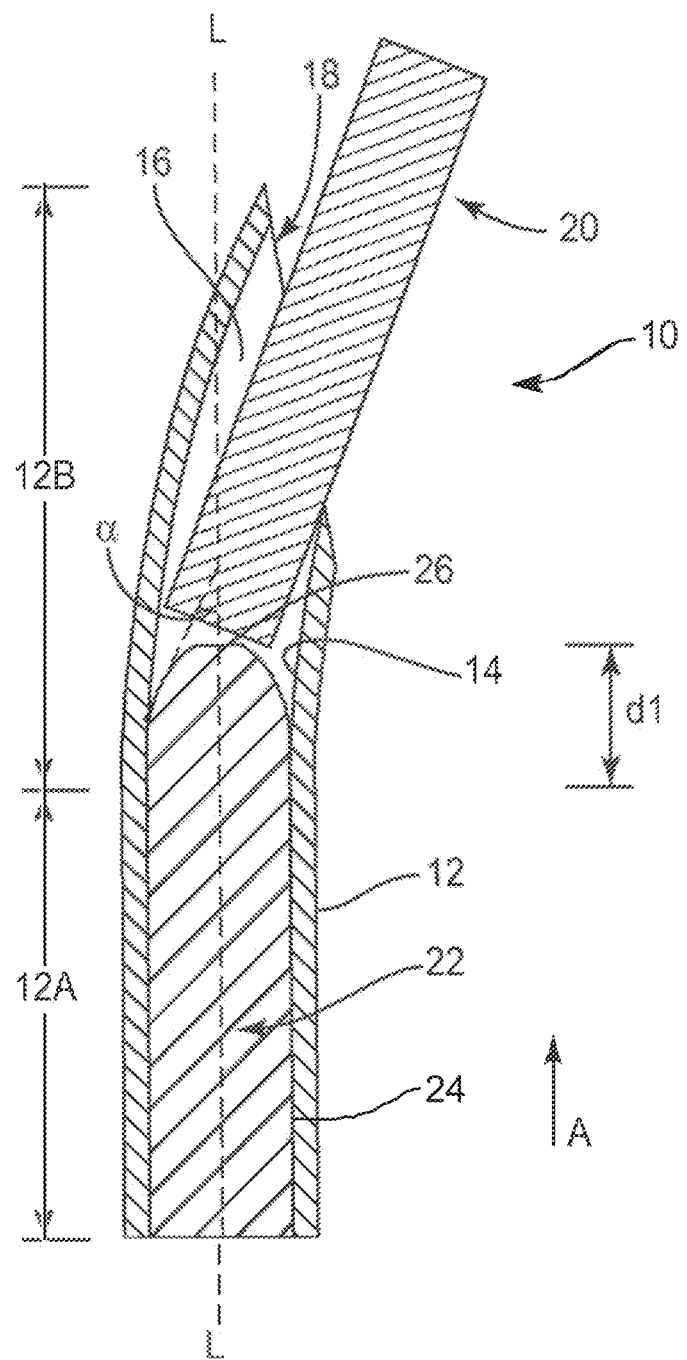
FIG. 1 is a cross-sectional view of a drug depot delivery system in accordance with the principles of the present disclosure.

The exemplary embodiments of a drug depot delivery system and related methods of use disclosed are discussed in terms of medical devices for the delivery of drug depots, such as, for example, pellets to a target site within a patient's anatomy. In some embodiments, the pellet delivery system comprises an injector assembly to store the pellets. In some embodiments, the drug depot delivery system comprises an epidural Tuohy needle to create a pathway to the epidural space. In another embodiment, the drug depot delivery system comprises a delivery plunger to transport the drug depot, such as pellets, through the system. In some embodiments, the pellets are 4 mm in length and 0.75 mm in diameter and require a sturdy delivery plunger stylet to push them through the injector assembly. In some embodiments, the epidural Tuohy needle has a curved tip that will not allow the stylet tip to reach the opening of the Tuohy's cannula.

This could result in the drug depots remaining inside the cannula instead of being delivered to the patient, particularly when more than one drug depot is being delivered. In order to ensure full deployment from the delivery plunger, the stylet has an enhanced "bullet-nose" feature. This feature elongates the stylet plunge depth by fitting a chamfer or radius to the edge of the tip and extending the point at which the curve impedes the stylet further down the shaft. That is, the elongated chamfer or radius at the tip of the stylet creates a bullet-like shape to allow the stylet to travel further down the curved tip of the epidural Tuohy needle cannula, decreasing the risk of the drug depots, such as pellets, remaining inside the cannula during deployment.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The pellet delivery system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. For example, a reference to "a drug depot" refers to one or a plurality of drug depots. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may comprise administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment comprises preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically comprises procedures that have only a marginal effect on the patient. Treatment can comprise inhibiting the disease, e.g., arresting its development, or relieving the disease, e.g., causing regression of the disease. For example, treatment can comprise reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" comprises soft tissue, ligaments, tendons, cartilage and/or bone unless specifically referred to otherwise.

The following discussion includes a description of a drug depot delivery system, related components and methods of employing the delivery system in accordance with the principles of the present disclosure. Alternate embodiments are also disclosed. Reference is made in detail to the exemplary embodiments of the present disclosure, which are illustrated in the accompanying figures. Turning to FIG. 1, there are illustrated components of a drug depot delivery system 10.

The components of drug depot delivery system 10 can be fabricated from biologically acceptable materials suitable for medical applications, including metals, synthetic polymers, ceramics and bone material and/or their composites. For example, the components of drug depot delivery system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO.sub.4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TOP), hydroxyapatite (HA)-TCP, calcium sulfate, or other resorbable polymers such as polyaetide, polyglycolide, polytyrosine carbonate, polycaroplaetohe and their combinations.

Various components of drug depot delivery system 10 may have material composites, including the above materials, to achieve various desired characteristics such as strength, rigidity, elasticity, compliance, biomechanical performance, durability and radiolucency or imaging preference. The components of drug depot delivery system 10, individually or collectively, may also be fabricated from a heterogeneous material such as a combination of two or more of the above-described materials. The components of drug depot delivery system 10 may be monolithically formed, integrally connected or comprise fastening elements and/or instruments, as described herein.

In some embodiments, drug depot delivery system 10 comprises a cannula or needle, such as, for example, an epidural Tuohy needle 12. Needle 12 is configured to create a pathway in a patient to a target area within the patient's anatomy, such as, for example, an epidural space of the patient. Needle 12 comprises an inner surface defining a passageway 16. Needle 12 comprises a first portion 12A that extends parallel to a longitudinal axis L and a curved second portion 12B comprising an opening 18 that is in communication with passageway 16. Second portion 12B extends transverse to longitudinal axis L.

In some embodiments, second portion 12B is continuously curved. In some embodiments, passageway 16 has a uniform diameter along its entire length. In some embodiments, passageway 16 may have various cross section configurations, such as, for example, oval, oblong, triangular, rectangular, square, polygonal, irregular, uniform, non-uniform, variable, tubular and/or tapered. In some embodiments, first portion 12A and/or second portion 12B may be disposed at alternate orientations, relative to longitudinal axis L, such as, for example, transverse, perpendicular and/or other angular orientations such as acute or obtuse, co-axial and/or may be offset or staggered. In some embodiments, needle 10 comprises a rigid material such that needle 10 cannot be bent without breaking. In some embodiments, needle 10 comprises a flexible material such that needle 10 can be bent without breaking.

Needle 12 is configured for disposal of a drug depot, such as, for example, a pellet 20 in passageway 60 such that pellet 20 can be pushed through passageway 16 and out of opening 18 for delivery to a target site within the anatomy of a patient. That is, pellet 20 is configured to be movably disposed in passageway 60. In some embodiments, a drug depot may comprise one or a plurality of pellets 20. Pellet 20 can exist in a solid drug form. When one or more pellets are used, the pellets can comprise more than one drug. Pellet 20 comprises at least one drug. In one embodiment, pellet 20 comprises a therapeutically effective amount of clonidine and a biodegradeable polymer. However, it is envisioned that the drug depots used can comprise any drug or combination of drugs and any polymer or combination of polymers, such as, for example, at least one biodegradable and/or bioresorbable polymer. In some embodiments, the drug depots may be variously shaped, such as, for example, cylindrical, oval, oblong, triangular, square, polygonal, irregular, uniform, non-uniform, offset, staggered, undulating, arcuate, variable and/or tapered. In some embodiments, pellet 20 is about 4 mm in length and about 0.75 mm in diameter. In some embodiments, the pellet 20 has a maximum diameter that is only slightly less than that of passageway 16 (e.g., about 0.01" to about 0.1" less than the maximum diameter of passageway 16) such that the outer surface of pellet 20 contacts inner surface 14 as pellet 20 moves through passageway 16. In some embodiments, pellet 20 has a maximum diameter that is about 0.2" to about 0.5" less than the maximum diameter of passageway 16 than that of passageway 16 such that the outer surface of pellet 20 is spaced apart from inner surface 14 as pellet 20 moves through passageway 16.

A stylet, such as, for example, a plunger 22 is slidably positioned in passageway 16 and comprises a shaft 24 having a tip 26 at a distal end of shaft 24. In some embodiments, plunger 22 is removable from passageway 16. Tip 26 is configured to push drug depot 20 through first and second portions 12A, 12B and out of opening 18 without drug depot 20 becoming stuck within passageway 16 or opening 18. In some embodiments, tip 26 is rounded. Tip 26 comprises an elongated chamfer or radius that defines a bullet-nose feature of tip 26. In some embodiments, tip 26 is hemispherical and is free of any planar surfaces. Chamfer extends at an angle α relative to longitudinal axis L, as shown in FIG. 1. In some embodiments, angle α is between about 10° and about 45° and all combinations and subcombinations therein. In some embodiments, angle α is about 35°.

Tip 26 is fixed relative to shaft 24 such that tip 26 cannot move relative to shaft 24. In some embodiments, tip 26 is monolithically and/or integrally famed with shaft 24. In some embodiments, plunger 22 comprises a rigid material such that plunger 22 cannot be bent without breaking. In some embodiments, tip 26 comprises the same material as shaft 24. In some embodiments, tip 26 has a maximum diameter that is less than that of shaft 24. In some embodiments, passageway 16 has an inner diameter that is greater than an outer diameter of shaft 24 such that an outer surface of shaft 24 slidably engages inner surface 14. In some embodiments, shaft 24 has a maximum diameter that is only slightly less than that of passageway 16 (e.g., about 0.01" to about 0.1" less than the maximum diameter of passageway 16) such that the outer surface of shaft 24 contacts inner surface 14 as shaft 24 moves through passageway 16. In some embodiments, shaft 24 has a maximum diameter that is about 0.2" to about 0.5" less than the maximum diameter of passageway 16 than that of passageway 16 such that the outer surface of shaft 24 is spaced apart from inner surface 14 as shaft 24 moves through passageway 16.

Figure 2:
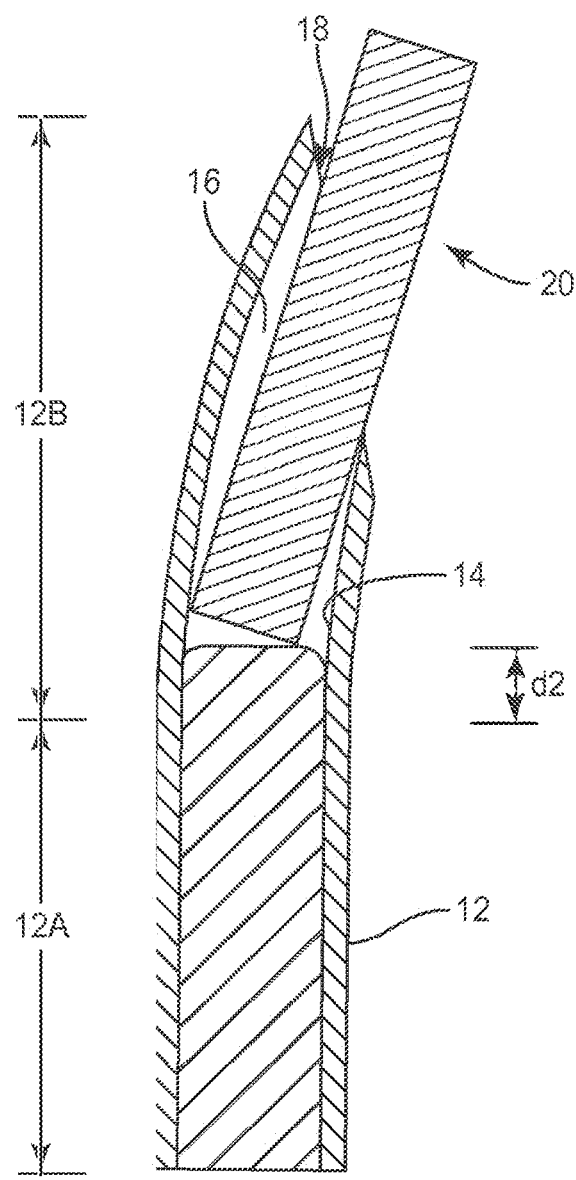
FIG. 2 is a cross-sectional view of a prior art system.

The bullet-nose feature of tip 26 allows tip 26 to move into second portion 12B of passageway 16 a greater distance than prior art tips that comprise an end surface that is planar. For example, as shown in FIG. 1, the bullet-nose feature of tip 26 allows tip 26 to move into second portion 12B of passageway 16 a distance d1, which allows tip 26 to move into second portion 12B of passageway 16 far enough to push pellet 20 out of opening 18 without pellet 20 becoming jammed within passageway 16. As shown in FIG. 2, prior art plungers have tips that comprise an end surface that is planar only allow the tip to move into second portion 12B of passageway 16 a distance d2, which is less than distance d1, and does not allow tip 26 to move into second portion 12B of passageway 16 far enough to push pellet 20 out of opening 18 without pellet 20 and subsequent pellets becoming jammed within passageway 16. That is, the likelihood of pellet 20 and subsequent pellets becoming jammed within passageway 16 is increased when the prior art tip is used versus tip 26.

In operation and use, needle 12 is used to create a pathway in a patient to a target area within the patient's anatomy, such as, for example, an epidural space of the patient. Needle 12 is advanced through the pathway until opening 18 is positioned in or adjacent to the target area. One or more drug depots such as pellet 20 are loaded into passageway 16. Shaft 24 is slidably positioned within passageway 16 such that tip 26 contacts one of pellet(s) 20. Shaft 24 is advanced through passageway 16 in the direction shown by arrow A in FIG. 1 such that at least one of pellet 20 exits passageway 16 through opening 18 to deliver at least one of pellet 20 to the target site without becoming jammed within passageway 16. In some embodiments, more than one pellet 20 will be within the passageway 16 next to one another and the shaft 24 will be advanced such that the second pellet 20 will exit the passageway 20 without being stuck within the passageway or behind the first pellet 20, the first pellet 20 having been successfully expelled. Shaft 24 may be withdrawn from passageway 16. Needle 12 may then be withdrawn from the pathway.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A drug delivery system, the system comprising:
   an epidural Tuohy needle configured to create a pathway to an epidural space, the needle comprising:
   a straight, proximal portion,
   a curved tip that extends transverse to a longitudinal axis of the straight, proximal portion, the curved tip comprising an opening, and
   a passageway in communication with the opening; and
   a plurality of solid drug pellets in the passageway, each of the solid drug pellets comprising a therapeutically effective amount of clonidine and a biodegradable polymer;
   a rigid plunger slidable in the passageway and configured to push the plurality of solid drug pellets through the passageway and out of the opening, the plunger comprising:
   a first end,
   a second end,
   a shaft portion extending from the first end to a position proximate the second end, and
   a tip portion extending from the position proximate the second end to the second end, the tip portion comprising a bullet-nose shape such that the tip portion has a radius of curvature from a maximum diameter at or adjacent the shaft portion to a minimum diameter at the second end such that a flat contact surface of the tip portion at the second end contacts and pushes the plurality of drug pellets through the passageway in the straight, proximal portion of the needle and such that a rounded contact surface of the tip portion contacts and pushes the plurality of drug pellets through the passageway in the curved tip of the needle and out of the opening of the needle.

2. The system of claim 1, wherein each of the plurality of solid drug pellets comprises:
   a length of 4 mm; and
   a diameter of 0.75 mm, a ratio of the length to the diameter being 5.33:1, the diameter being 0.01 inches to 0.1 inches less than a maximum diameter of the passageway or 0.2 inches to 0.5 inches less than a maximum diameter of the passageway.

3. The system of claim 1, wherein the plunger is configured to push the plurality of solid drug pellets through the passageway and out of the opening without the plurality of solid drug pellets becoming stuck in the passageway or the opening.

4. The system of claim 1, wherein the rounded contact surface of the tip portion allows the tip portion to move into the passageway a greater distance than if the tip portion comprised only a planar end surface.

5. A drug delivery system, the system comprising:
   a needle comprising:
   a straight, proximal portion,
   a curved tip, the curved tip comprising an opening, and
   a passageway in communication with the opening;
   a drug depot positioned in the passageway, the drug depot comprising a therapeutically effective amount of clonidine and a biodegradable polymer; and
   a rigid plunger slidable in the passageway and the configured to push the drug depot through the passageway and out of the opening, the plunger comprising:
   a first end,
   a second end,
   a shaft portion extending from the first end to a position proximate the second end, and
   a tip portion extending from the position proximate the second end to the second end, the tip portion comprising a bullet-nose shape such that the tip portion has a planar contact surface that is configured to contact and push the drug depot through the passageway in the straight, proximal portion of the needle and a rounded contact surface proximal to the planar contact surface that is configured to contact and push the drug depot through the passageway in the curved tip of the needle and out of the opening of the needle.

6. The system of claim 5, wherein the drug depot comprises a solid pellet having a length of 4 mm and a diameter of 0.75 mm, a ratio of the length to the diameter being 5.33:1, the diameter being 0.01 inches to 0.1 inches less than a maximum diameter of the passageway or 0.2 inches to 0.5 inches less than a maximum diameter of the passageway.

7. The system of claim 5, wherein the drug depot comprises a plurality of pellets.

8. The system of claim 7, wherein each of the plurality of pellets comprises:
   a length of 4 mm;
   a diameter of 0.75 mm, the diameter being 0.01 inches to 0.1 inches less than a maximum diameter of the passageway or 0.2 inches to 0.5 inches less than a maximum diameter of the passageway.

9. The system of claim 5, wherein the plunger is configured to push the drug depot through the passageway and out of the opening without the drug depot becoming stuck in the passageway or the opening.

10. The system of claim 5, wherein a chamfer angle of the tip portion is 10° to 45°.

11. The system of claim 5, wherein the plunger is configured to push the drug depot through the passageway and out of the opening without the drug depot becoming stuck in the passageway or the opening, wherein the needle is an epidural Tuohy needle configured to create a pathway to an epidural space, wherein the plunger is rigid, and wherein the drug depot comprises a solid pellet having a length of 4 mm and a diameter of 0.75 mm.

12. A drug delivery system, the system comprising:
    a plunger slidable in a passageway of a needle having a straight, proximal portion, a curved distal tip comprising an opening, the passageway being in communication with the opening, the plunger configured to push a drug depot through the passageway and out of the opening, the plunger comprising:
a first end,
a second end,
a shaft portion extending from the first end to a position proximate the second end, and
a tip portion extending from the position proximate the second end to the second end, the tip portion comprising a bullet-nose shape such that the tip portion comprises a planar distal contact surface that is configured to contact and push the drug depot through the passageway in the straight, proximal portion of the needle and a contact surface proximal to the planar contact surface that has a radius of curvature or chamfer angle, wherein the contact surface proximal to the planar contact surface is configured to contact and push the drug depot through the passageway in the curved distal tip of the needle and out of the opening of the needle.

13. The system of claim 12, further comprising the drug depot positioned in the passageway.

14. The system of claim 13, wherein the drug depot comprises a therapeutically effective amount of clonidine and a biodegradable polymer.

15. The system of claim 13, wherein the drug depot comprises a pellet having a length of 4 mm and a diameter of 0.75 mm.

16. The system of claim 13, wherein a ratio of a length of the drug depot to a diameter of the drug depot is 5.33:1.

17. The system of claim 13, wherein the drug depot comprises a plurality of pellets.

18. The system of claim 12, wherein the contact surface proximal to the planar contact surface has a chamfer angle and wherein the chamfer angle is 10° to 45° relative to a longitudinal axis of the plunger.

19. The system of claim 12, wherein the plunger is configured to push the drug depot through the passageway and out of the opening without the drug depot becoming stuck in the passageway or the opening.

20. The system of claim 12, further comprising the drug depot positioned in the passageway, wherein the drug depot comprises a therapeutically effective amount of clonidine and a biodegradable polymer, wherein a ratio of the length to the diameter being 5.33:1, and wherein the plunger is configured to push the drug depot through the passageway and out of the opening without the drug depot becoming stuck in the passageway or the opening.

* * * * *